United States Patent
Hieda et al.

(10) Patent No.: US 10,415,011 B2
(45) Date of Patent: Sep. 17, 2019

(54) ADHEREND RECOVERY METHOD, ADHEREND RECOVERY APPARATUS, GAS-GENERATING FILM AND RESIN COMPOSITION

(71) Applicant: JSR CORPORATION, Tokyo (JP)

(72) Inventors: Katsuhiko Hieda, Tokyo (JP); Tsutomu Shimokawa, Tokyo (JP); Hiroto Kubo, Tokyo (JP); Takashi Doi, Tokyo (JP)

(73) Assignee: JSR CORPORATION, Tokyo (JP)

( * ) Notice: Subject to any disclaimer, the term of this patent is extended or adjusted under 35 U.S.C. 154(b) by 780 days.

(21) Appl. No.: 15/051,681

(22) Filed: Feb. 24, 2016

(65) Prior Publication Data

US 2016/0168532 A1    Jun. 16, 2016

Related U.S. Application Data (63) Continuation of application No. PCT/JP2014/070686, filed on Aug. 6, 2014.

(30) Foreign Application Priority Data

Aug. 30, 2013 (JP) ................................. 2013-179121

(51) Int. Cl.
   *B32B 43/00* (2006.01)
   *C12N 1/02* (2006.01)
   (Continued)

(52) U.S. Cl.
   CPC .............. *C12N 1/02* (2013.01); *B32B 43/006* (2013.01); *C08J 5/18* (2013.01); *C08K 5/235* (2013.01);
   (Continued)

(58) Field of Classification Search
   CPC . Y10T 156/1147; B32B 43/006; C12M 33/00
   See application file for complete search history.

(56) References Cited

U.S. PATENT DOCUMENTS

| 4,275,142 A | 6/1981 | Hosaka et al. |
| 5,609,954 A * | 3/1997 | Aizawa ...................... C09J 7/38 |
| | | 428/317.5 |

(Continued)

FOREIGN PATENT DOCUMENTS

| JP | 352134656 | 11/1977 |
| JP | 03-152942 | 6/1991 |

(Continued)

OTHER PUBLICATIONS

"Search Report of Europe Counterpart Application", dated Mar. 21, 2017, p. 1-p. 7, in which the listed references were cited.

(Continued)

*Primary Examiner* — Mark A Osele
(74) *Attorney, Agent, or Firm* — JCIPRNET (57) ABSTRACT

The invention is an adherend recovery method capable of recovering adherends such as cells no matter the types of adherends.
An adherend recovery method for recovering an adherend from a support includes exposing a stack disposed on the support, the stack including a photosensitive gas generation layer, an adhesive layer and the adherend in this order on the support, generating a gas from the photosensitive gas generation layer by the exposure to separate the support and the stack from each other by the action of the gas, and recovering the adherend from the support by recovering the stack separated.

6 Claims, 3 Drawing Sheets

(51) Int. Cl.
*C12M 1/26* (2006.01)
*C08J 5/18* (2006.01)
*C08K 5/23* (2006.01)
*C08K 5/28* (2006.01)
*C12N 5/071* (2010.01)
*C12M 1/12* (2006.01)
*H01L 21/302* (2006.01)
*C12M 1/00* (2006.01)

(52) U.S. Cl.
CPC ............... *C08K 5/28* (2013.01); *C12M 25/06* (2013.01); *C12M 33/00* (2013.01); *C12N 5/0625* (2013.01); *H01L 21/302* (2013.01); *C08J 2333/02* (2013.01); *C12M 23/20* (2013.01); *Y10T 156/1147* (2015.01)

(56) References Cited

U.S. PATENT DOCUMENTS

| | | | |
|---|---|---|---|
| 6,399,267 | B1 | 6/2002 | Nishimura et al. |
| 7,371,300 | B2 * | 5/2008 | Bain .................. C08J 9/32 156/247 |
| 7,641,760 | B2 * | 1/2010 | Doi .................. B29C 63/0013 156/711 |
| 8,753,855 | B2 * | 6/2014 | Nakashima ............ C12M 25/14 435/173.9 |
| 9,434,936 | B2 * | 9/2016 | Sumaru .................. C12M 23/20 |
| 2003/0219889 | A1 | 11/2003 | Sumaru et al. |
| 2007/0037364 | A1 | 2/2007 | Sugita et al. |
| 2008/0073034 | A1 * | 3/2008 | Izutani .............. H01L 21/67132 156/752 |
| 2009/0305414 | A1 * | 12/2009 | Apostol ................ C08F 226/10 435/402 |
| 2010/0129985 | A1 * | 5/2010 | Ootake .................. C09J 7/35 438/464 |
| 2010/0279396 | A1 * | 11/2010 | Choi .................. C12M 23/16 435/294.1 |
| 2011/0014096 | A1 | 1/2011 | Fukuoka et al. |
| 2012/0225448 | A1 | 9/2012 | Sugiyama et al. |
| 2013/0295747 | A1 * | 11/2013 | Kim .................. C09J 133/066 438/464 |
| 2014/0011960 | A1 * | 1/2014 | Konno .................. C12M 25/02 525/326.8 |
| 2015/0225686 | A1 * | 8/2015 | Oshima .................. C12M 31/02 435/173.4 |

FOREIGN PATENT DOCUMENTS

| | | |
|---|---|---|
| JP | H08286384 | 11/1996 |
| JP | 2001-200234 | 7/2001 |
| JP | 2001281853 | 10/2001 |
| JP | 2002-286592 | 10/2002 |
| JP | 2003-339373 | 12/2003 |
| JP | 2003-342540 | 12/2003 |
| JP | 2005-191513 | 7/2005 |
| JP | 2006/288217 | 10/2006 |
| JP | 2009-45002 | 3/2009 |
| JP | 2010107515 | 5/2010 |
| JP | 2010-153774 | 7/2010 |
| JP | 2011-142115 | 7/2011 |
| JP | 2012188306 | 10/2012 |
| JP | 2013-071847 | 4/2013 |
| WO | 2011058721 | 5/2011 |
| WO | 2012121547 | 9/2012 |
| WO | WO-2015098919 A1 * | 7/2015 ............... C12N 1/02 |

OTHER PUBLICATIONS

"Office Action of Europe Counterpart Application," dated Sep. 11, 2018, p. 1-p. 6.

"Office Action of Japan Counterpart Application," with machine English translation thereof, dated Jul. 18, 2017, p. 1-p. 7, in which the listed references were cited.

* cited by examiner

ADHEREND RECOVERY METHOD, ADHEREND RECOVERY APPARATUS, GAS-GENERATING FILM AND RESIN COMPOSITION

CROSS REFERENCE TO RELATED APPLICATIONS

This application is a Continuation of PCT International Application No. PCT/JP2014/070686, filed on Aug. 6, 2014, which claims priority under 35 U.S.C. § 119(a) to Japanese Patent Application No. 2013-179121, filed on Aug. 30, 2013. Each of the above applications is hereby expressly incorporated by reference, in its entirety, into the present application.

TECHNICAL FIELD

The invention relates to an adherend recovery method, an adherend recovery apparatus and a resin composition.

BACKGROUND ART

In the field of regenerative medicine, somatic cells are cultured by inducing the differentiation of stem cells such as iPS cells and ES cells. Because iPS cells and ES cells are not homogeneous, somatic cells cultured from such cells are also inhomogeneous. Thus, techniques for selectively recovering the cells are studied.

The cell recovery techniques rely on such methods as flow cytometry and magnetic cell separation. These methods involve dispersing the cells in a solution and consequently cause a significant damage to the cells. To address this problem, Patent Literatures 1 to 3 propose that the recovery is made by the application of light so as to cause a change in the adhesive layer to which the cells adhere.

CITATION LIST

Patent Literature

Patent Literature 1: JP-A-2002-286592
Patent Literature 2: JP-A-2006-288217
Patent Literature 3: JP-A-2003-339373

SUMMARY OF INVENTION

Technical Problem

The fact that the methods of Patent Literatures 1 to 3 give rise to a change in the adhesive layer sometimes inhibits the methods from being applied to anchorage-dependent cells. Further, the fact that the surface to which cells adhere undergoes a change may cause a damage to the cells.

The invention provides an adherend recovery method capable of recovering adherends such as cells no matter the types of adherends.

Solution to Problem

For example, aspects of the invention reside in [1] to [12] below.

[1] An adherend recovery method for recovering an adherend from a support, including:
a step (I) of exposing a stack disposed on the support, the stack including a photosensitive gas generation layer, an adhesive layer and the adherend in this order on the support, a step (II) of generating a gas from the photosensitive gas generation layer to separate the support and the stack from each other by the action of the gas, and a step (III) of recovering the adherend from the support by recovering the stack separated.

[2] The adherend recovery method described in [1], wherein the photosensitive gas generation layer includes at least one selected from azides and diazo compounds.

[3] The adherend recovery method described in [1] or [2], wherein the photosensitive gas generation layer includes an elastomer.

[4] The adherend recovery method described in [1] or [2], wherein the photosensitive gas generation layer includes a polymer containing a (meth)acrylic structural unit.

[5] The adherend recovery method described in [4], wherein the photosensitive gas generation layer comprises 5 to 20 parts by mass of the at least one selected from azides and diazo compounds based on 100 parts by mass of the polymer containing a (meth)acrylic structural unit.

[6] The adherend recovery method described in [1] to [5], wherein the adherend is a cell.

[7] The adherend recovery method described in [1] to [4] wherein a plurality of stacks are disposed on the support and a desired adherend is selectively recovered from the support by selectively exposing the target stack.

[8] An adherend recovery apparatus including:
(1) a substrate including a stack, the stack includes a support, a photosensitive gas generation layer and an adhesive layer in this order,
(2) a stage on which the substrate is placed,
(3) a device configured to supply a target substance to the substrate,
(4) a detection device configured to provide information of the position of the adherend (target substance),
(5) an exposure device configured to expose the photosensitive gas generation layer, and
(6) a control device configured to control the members (1) to (5).

[9] A resin composition including a polymer containing a (meth)acrylic structural unit, and at least one selected from azides and diazo compounds.

[10] The resin composition described in [9], including 5 to 20 parts by mass of the at least one selected from azides and diazo compounds based on 100 parts by mass of the polymer containing a (meth)acrylic structural unit.

[11] A gas-generating film including a polymer containing a (meth)acrylic structural unit, and at least one selected from azides and diazo compounds.

[12] The gas-generating film described in [11], including 5 to 20 parts by mass of the at least one selected from azides and diazo compounds based on 100 parts by mass of the polymer containing a (meth)acrylic structural unit.

Advantageous Effects of Invention

According to the invention, adherends such as cells can be recovered no matter the types of adherends.

DESCRIPTION OF EMBODIMENTS

The adherend recovery method of the invention recovers an adherend from a support.

The method includes exposing a stack disposed on the support (step (1)), the stack including a photosensitive gas generation layer, an adhesive layer and the adherend in this order on the support; generating a gas from the photosensitive gas generation layer to separate the support and the stack from each other by the action of the gas (step (2)); and recovering the adherend from the support by recovering the stack separated (step (3)).

Figure 1:
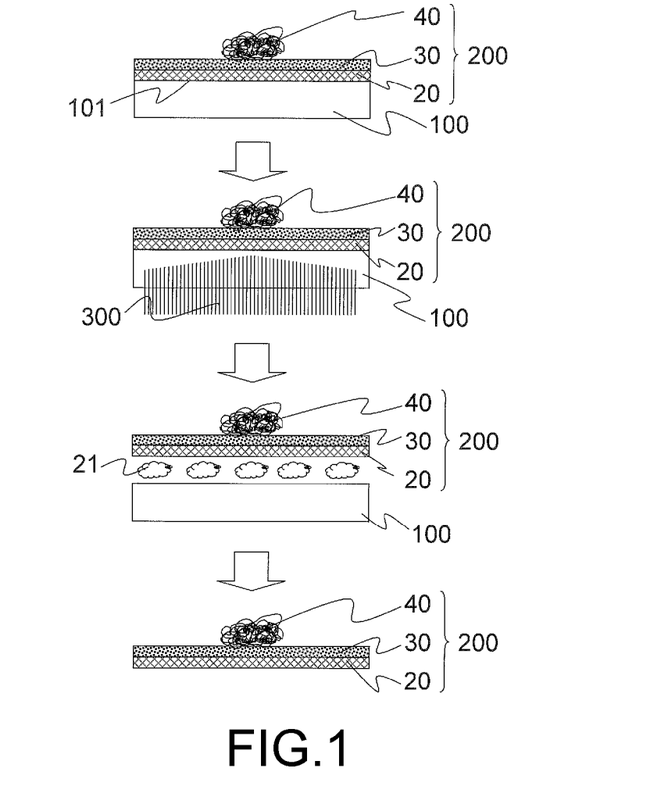
FIG. 1 is a schematic view illustrating an adherend recovery method of the invention.

The adherend recovery method is schematically illustrated in FIG. 1.

In a conventional recovery method, an adhesive layer to which a target substance is attached has a function to bond the adherend and also a function to be chemically changed by irradiation. This fact gives rise to a problem that the adherend is damaged by the chemical change. The invention involves a photosensitive gas generation layer which has a function to be chemically changed by irradiation, in combination with an adhesive layer which serves to bond the adherend. This configuration eliminates the risk for the adherend to be damaged by the chemical change. The adhesive layer may be selected appropriately in accordance with the types of adherend to be attached. Thus, the method can be applied even to the recovery of adherends which adheres to a limited type of an adhesive layer such as when the adherend is a biological substance such as anchorage-dependent cells. The adherend may be recovered without being damaged because of the facts that the phenomenon resulting from the chemical change is the generation of gas, and that the influence of the gas is produced between the support and the photosensitive gas generation layer and this affected region is isolated from the adherend and the adhesive layer.

1. Step (1)

In the step (1), a stack 200 disposed on a support 100 which includes a photosensitive gas generation layer 20, an adhesive layer 30 and an adherend 40 in this order is exposed.

The support 100 may be any rigid or flexible material as long as it can hold the stack 200. Examples of the supports 100 include those including such materials as silicon, glass, quarts, silicon carbide, silicon nitride, acrylic resin, polycarbonate, polycycloolefin, polyimide and polystyrene. In particular, preferred supports are those including materials which have a high transparency with respect to exposure light 300 such as glass, quarts, silicon carbide, acrylic resin, polycarbonate, polycycloolefin and polystyrene.

Figure 2:
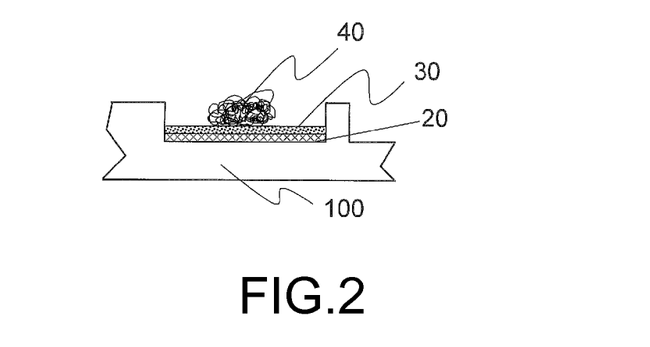
FIG. 2 is a schematic view illustrating an example of supports.

The shape of the support 100 is not limited as long as the support has a surface 101 which allows the stack 200 to be supported thereon. The surface of the support may or may not be flat. For example, the support may be a flat plate or, as illustrated in FIG. 2, may have a recess. The thickness of the support is usually 1 μm to 1 mm and may be selected appropriately in accordance with the purpose such as the desired use application. Connection ports such as inlets and outlets for establishing connections to external members may be provided in the supports 100.

The surface 101 of the support 100 on which the stack 200 is placed may have a surface modification layer. Examples of the surface modification layers include layers obtained by treating the surface 101 with a coupling agent such as 3-aminopropyltrimethoxysilane, 3-aminopropyltriethoxysilane or hexamethyldisilazane to enhance the adhesion between the support 100 and the stack 200; and layers obtained by treating the surface 101 with a release agent such as a silicone release agent or a fluorine release agent to decrease the adhesion between the support 100 and the stack 200.

The stack 200 includes a photosensitive gas generation layer 20, an adhesive layer 30 and an adherend 40 in this order. The thickness of the stack 200 is usually 1 μm to 1 cm and may be selected appropriately in accordance with the type of the adherend 40.

The stack 200 may be placed on the support 100 by stacking the photosensitive gas generation layer 20, the adhesive layer 30 and the adherend 40 in this order on the surface 101 of the support 100 for the placement of the stack 200.

Figure 3:
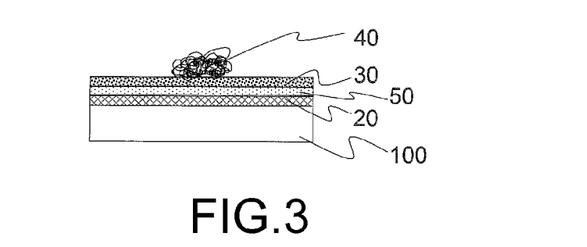
FIG. 3 is a schematic view illustrating an example of stacks.

As illustrated in FIG. 3, a gas barrier layer 50 may be provided between the photosensitive gas generation layer 20 and the adhesive layer 30. The gas barrier layer 50 serves so that a gas 21 generated by the photosensitive gas generation layer 20 will be discharged on the support 100 side. Examples of the gas barrier layers 50 include those including such materials as polyacrylics, polyolefins, polycarbonates, vinyl chloride resins, ABS resins, polyethylene terephthalate resins, nylon resins, urethane resins, polyimide resins and glass. The thickness of the gas barrier layer 50 is usually 1 μm to 1 mm and may be selected appropriately in accordance with factors such as the material of the gas barrier layer 50 and the type of the gas 21.

Examples of the exposure light 300 usually include ultraviolet rays and visible rays. Specifically, the light has a wavelength of 200 to 500 nm (for example, i-line wavelength (365 nm)) and may be selected appropriately in accordance with the type of the photosensitive gas generation layer 20. The exposure light may be laser light or may include a plurality of wavelengths. The active light irradiation dose may be selected appropriately in accordance with factors such as the type and thickness of the photosensitive gas generation layer 20. When the i-line wavelength is used as the exposure light, the exposure dose is usually 100 to 1500 mJ/cm$^2$.

Figure 4:
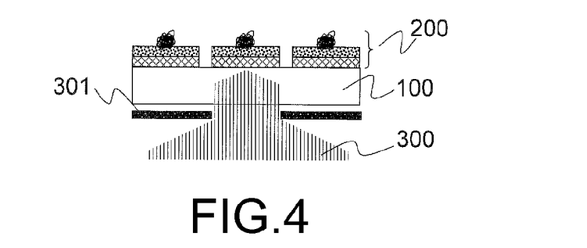
FIG. 4 is a schematic view illustrating an example of a process in which a desired stack of a plurality of stacks is exposed.

In the case where a plurality of stacks 200 are disposed on the support 100 and the desired stack 200 is selectively exposed, the stack 200 of interest may be exposed individually or, for example, exposure may be applied through a mask 301 having an opening only in the region corresponding to the desired stack 200 as illustrated in FIG. 4. In the similar manner, a portion of the stack 200 may be exposed through such a mask 301. For example, exposure may be applied with use of a contact aligner, a stepper or a scanner.

The stack 200 may be exposed in any direction through the adherend 40 side or the support 100 side. In particular, the stack 200 is suitably exposed through the support 100 side to eliminate the risk of damaging the adherend 40 with the exposure light 300. When the stack 200 is exposed through the support 100 side, it is preferable that the support 100 be made of a material having a high transparency to the exposure light 300.

1-1. Photosensitive Gas Generation Layers

The photosensitive gas generation layer 20 includes a photosensitive gas generator that generates a gas when irradiated. The photosensitive gas generation layer 20 may include additional components other than the photosensitive gas generator such as a binder resin to compensate the photosensitive gas generator. The photosensitive gas generator is a substance that is photoreacted or oxidatively decomposed to generate a gas when irradiated with light having a prescribed wavelength. Such photosensitive gas generators that generate a gas by oxidative decomposition are used together with photocatalysts such as titanium oxide, and generate a gas by being decomposed by the oxidative action of the photocatalysts.

Examples of the photosensitive gas generators that generate a gas by photoreaction include azides, diazo compounds, azo compounds, diazonium salts, sulfohydrazide compounds, hydrazo compounds, nitrobenzyl carbamate compounds, benzoin carbamate compounds and diazomethane sulfonate compounds. Of these, azides and diazo compounds, and nitrobenzyl carbamate compounds and benzoin carbamate compounds are advantageous in that they generate inert gas as the gas 21 and do not cause a damage to the adherend 40 or the adhesive layer 30, wherein azides and diazo compounds generate nitrogen and nitrobenzyl carbamate compounds and benzoin carbamate generate carbon dioxide. In particular, an azide is preferable when the generator is used in combination with an elastomer as the binder resin described later. When the generator is used in combination with a polymer containing a (meth)acrylic monomer unit as the binder resin, at least one selected from azides and diazo compounds is preferable. Azides and diazo compounds can separate the support 100 and the stack 200 efficiently because these photosensitive gas generators generate a gas in a volume approximately 2 to 100 times the volume of the generator.

Examples of the azides include those compounds described in JP-A-2013-071847 and JP-A-2010-153774. Specific examples include 4,4'-diazidodiphenylsulfone, 3,3'-diazidodiphenylsulfone, 3,4'-diazidodiphenylsulfone, 4,4'-diazidostilbene, 1,3-bis-(4'-azidobenzal)-acetone, 1,3-bis-(4'-azidocinnamylidene)-2-propanone, 4,4'-diazidochalcone, 2,6-bis-(4'-azidobenzal)-cyclohexanone, 2,6-bis-(4'-azidobenzal)-4-methylcyclohexanone, 2,6-bis-(4'-azidobenzal)-4-tert-butylcyclohexanone, 4-azidoacetophenone, 4-azidobenzalacetophenone, 4-azidobenzalacetone, 4-azidobenzaldehyde and 4-azidobenzoic acid.

Examples of the diazo compounds include diazomethane, diazodinitrophenol, bis(trifluoromethylsulfonyl)diazomethane, bis(cyclohexylsulfonyl)diazomethane, bis(phenylsulfonyl)diazomethane, bis(p-toluenesulfonyl)diazomethane, methylsulfonyl-p-toluenesulfonyldiazomethane, 1-cyclohexylsulfonyl-1-(1,1-dimethylethylsulfonyl)diazomet bane, bis(1,1-dimethylethylsulfonyl)diazomethane, 4-diazo-1-dimethylaminobenzene, 4-diazo-1-diethylaminobenzene, 4-diazo-1-dipropylaminobenzene, 4-diazo-1-methylbenzylaminobenzene, 4-diazo-1-dibenzylaminobenzene, 4-diazo-1-ethylhydroxyethylaminobenzene, 4-diazo-1-diethylamino-3-methoxybenzene, 4-diazo-1-dimethylamino-2-methylbenzene, 4-diazo-1-benzoylamino-2,5-diethoxybenzene, 4-diazo-1-morpholinobenzene, 4-diazo-1-morpholino-2,5-diethoxybenzene, 4-diazo-1-morpholino-2,5-dibutoxybenzene, 4-diazo-1-toluylmercapto-2,5-diethoxybenzene, 4-diazo-1,4-methoxybenzoylamino-2,5-diethoxybenzene, and 1,2-naphthoquinonediazido-4-sulfonate esters and 1,2-naphthoquinonediazido-5-sulfonate esters of compounds such as 4,4'-dihydroxydiphenylmethane, 4,4'-dihydroxydiphenyl ether, 2,3,4-trihydroxybenzophenone, 2,3,4,4'-tetrahydroxybenzophenone, 2,3,4,2',4'-pentahydroxybenzophenone, tris(4-hydroxyphenyl)methane, tris(4-hydroxyphenyl)ethane, 1,1-bis(4-hydroxyphenyl)-1-phenylethane, 1,3-bis[1-(4-hydroxyphenyl)-1-methylethyl]benzene, 1,4-bis[1-(4-hydroxyphenyl)-1-methylethyl]benzene, 4,6-bis[1-(4-hydroxyphenyl)-1-methylethyl]-1,3-dihydroxybenzene and 1,1-bis(4-hydroxyphenyl)-1-[4-{1-(4-hydroxyphenyl)-1-methylethyl}phenyl]ethane.

Examples of the photosensitive gas generators that generate a gas by oxidative decomposition include those compounds having functional groups readily oxidized by the action of the photocatalysts such as carboxylic acid groups, aldehyde groups and primary alcohol groups. Upon oxidation, these types of compounds generate carbon dioxide as the gas.

The photosensitive gas generators may be used singly, or two or more may be used in combination.

The photosensitive gas generation layer 20 may include a component such as a binder resin to hold the photosensitive gas generator in the photosensitive gas generation layer 20. The binder resin is used to compensate the photosensitive gas generator and to hold the photosensitive gas generator in the photosensitive gas generation layer 20.

Figure 5:
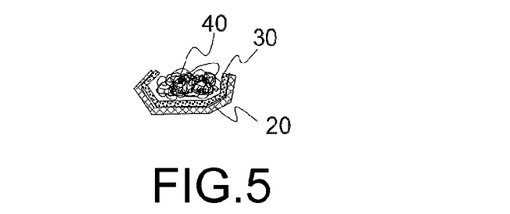
FIG. 5 is a schematic view illustrating an example of stacks after exposure.

Examples of the binder resins include cycloolefin polymers, polyethers, polycarbonates, polystyrenes, polyimides, phenolic resins, petroleum resins, elastomers and acrylic resins. Of these, elastomers are preferable because, as illustrated in FIG. 5, they shrink in the presence of stress so as to wrap the adherend 40. Of the binder resins, acrylic resins are preferable because they have low gas permeability and the generated gas can be trapped efficiently.

Examples of the elastomers include natural rubbers, styrene isoprene rubbers, styrene butadiene rubbers, butadiene rubbers, ethylene propylene rubbers, urethane rubbers and cyclized forms of these rubbers having a ring structure.

Examples of the cyclized rubbers include cyclized natural rubbers, cyclized polyisoprenes, cyclized polyisobutylenes and cyclized polybutadienes.

The acrylic resins are polymers obtained using at least one monomer selected from (meth)acrylic acid and (meth)acrylate esters. Examples of the (meth)acrylate esters include phenoxydiethylene glycol (meth)acrylate, phenoxytriethylene glycol (meth)acrylate, phenoxytetraethylene glycol (meth)acrylate, phenoxypolyethylene glycol (meth)acrylate, phenoxydipropylene glycol (meth)acrylate, phenoxytripropylene glycol (meth)acrylate, phenoxytetrapropylene glycol (meth)acrylate, lauroxydiethylene glycol (meth)acrylate, lauroxytriethylene glycol (meth)acrylate, lauroxytetraethylene glycol (meth)acrylate, lauroxydipropylene glycol (meth)acrylate, lauroxytripropylene glycol (meth)acrylate, lauroxytetrapropylene glycol (meth)acrylate, methyl (meth)acrylate, ethyl (meth)acrylate, n-propyl (meth)acrylate, n-butyl (meth)acrylate, 2-hydroxyethyl (meth)acrylate, 2-hydroxypropyl (meth)acrylate, polyethylene glycol mono (meth)acrylate, polypropylene glycol mono(meth)acrylate, glycerol mono(meth)acrylate, phenyl (meth)acrylate, benzyl (meth)acrylate, cyclohexyl (meth)acrylate, isobornyl (meth)acrylate and tricyclodecanyl (meth)acrylate.

The content of the structural units derived from the (meth)acrylate monomer in the acrylic resin is 50 mass % or above, preferably 70 mass % or above, and more preferably 90 mass % or above. This content ensures that the desirable gas permeability is accomplished.

When the photosensitive gas generation layer 20 includes the photosensitive gas generator and the binder resin, the content of the photosensitive gas generator is 0.1 to 1000 parts by mass, preferably 0.5 to 100 parts by mass, more preferably 1 to 50 parts by mass, and still more preferably 5 to 20 parts by mass based on 100 parts by mass of the binder resin. This content ensures that the stack 200 may be efficiently separated from the support 100. The content of the photosensitive gas generator and the binder resin in the photosensitive gas generation layer 20 is 1 to 99 wt %, and preferably 50 to 99 wt %. This content ensures that the stack 200 may be efficiently separated from the support 100.

The most preferred combination of the photosensitive gas generator and the binder resin is a combination of an azide and an elastomer, a combination of an azide and an acrylic resin, or a combination of a diazo compound and an acrylic resin. When exposed, the azide generates a gas and also reacts with the elastomer to form a crosslinked structure. Thus, the exposure results in a shrinkage of the photosensitive gas generation layer 20. Consequently, as illustrated in FIG. 5, the stack 200 shrinks so as to wrap the adherend 40. This structure allows for efficient recovery of the adherend 40 from the support 100. The acrylic resin has low gas permeability and can trap the generated gas efficiently, thereby allowing the adherend to be recovered from the support efficiently.

The photosensitive gas generation layer 20 may contain additives such as leveling agents, plasticizers, surfactants, antifoaming agents, sensitizers, halation inhibitors and storage stabilizers while ensuring that the functions of the photosensitive gas generation layer 20 are not impaired.

For example, the photosensitive gas generation layer 20 may be formed by applying a composition including the photosensitive gas generator and optionally a solvent onto the surface 101 of the support 100 for the placement of the stack 200, by an application method such as a spin coating method, an inkjet method, a spray coating method or a bar coating method. A resin composition used to form the photosensitive gas generation layer 20 of the invention includes the polymer containing a (meth)acrylic structural unit, and at least one selected from the azides and the diazo compounds. The thickness of the gas generation layer is selected appropriately in accordance with factors such as the application method and the content of the photosensitive gas generator. The thickness may be usually 1 μm or more. After the composition is applied, for example, the coating may be heated with a device such as a hot plate. The heating conditions are usually 20 to 200° C. and 1 to 600 seconds.

The solvent is not limited as long as it can efficiently dissolve the components for the composition. When the azide is added to the composition, the solvent is preferably an ether solvent such as tetrahydrofuran, diethyl ether or diethylene glycol diethyl ether, an aromatic solvent such as toluene, benzene or xylene, or a ketone solvent such as methyl ethyl ketone, methyl amyl ketone, cyclopentanone or cyclohexanone. When the diazo compound is added to the composition, the solvent is preferably an ester solvent such as ethyl lactate, ethyl acetate or propylene glycol monomethyl ether acetate.

The photosensitive gas generation layers may be applied to use as gas-generating films. Such gas-generating films include, as described hereinabove, a polymer containing a (meth)acrylic structural unit, and at least one selected from azides and diazo compounds. The film thickness is not particularly limited and is selected appropriately in accordance with the purpose. The films may be dependent films or may be formed on the surface of release bases and transferred to workpieces.

1-2. Adhesive Layers

The adhesive layer 30 is used to bond the adherend 40. The type of the adhesive layer 30 may be selected appropriately in accordance with the type of the adherend 40. The adhesive layer 30 is not limited as long as it includes a material exhibiting adhesion with respect to the adherend 40. In the case where the adherends 40 are inorganic materials such as semiconductor devices, examples of the adhesive materials include those materials generally used for the bonding of inorganic materials such as epoxy resins, acrylic resins and phenolic resins. When the adherends 40 are biological substances, examples of the adhesive materials include those materials exhibiting adhesion with respect to the desired biological substances such as culture media for culturing general biological substances.

Examples of the materials exhibiting adhesion with respect to biological substances include non-biological substances such as various glasses, aluminum oxide, quartz, gold and plasma-treated polystyrene; basic substances such as hydrophilic polystyrene, polylysine, aminopropyltriethoxysilane and N-(2-aminoethyl)-3-aminopropyltrimethoxysilane, and condensates of these basic substances; and biological substances such as fibronectin, laminin, tenascin, vitronectin, peptide, collagen, atelocollagen, gelatin, fibrous protein, glycoprotein, glucosaminoglycan, proteoglycan, fibronectin, hyaluronic acid, entactin and chondroitin sulfate proteoglycan, and composites of these biological substances such as extracellular matrixes.

As long as the adhesion to the adherend 40 is not impaired, the adhesive layer 30 may contain additives such as leveling agents, plasticizers, surfactants, antifoaming agents and sensitizers, and binder resins such as polyvinyl alcohol, unsaturated polyester, acrylic resin, polyethylene, diallyl phthalate, ethylene propylene diene monomer, epoxy resin, phenolic resin, polyurethane, melamine resin, polycarbonate, polyvinyl chloride, polyamide, polyimide, styrene butadiene rubber, chloroprene rubber, polypropylene, polybutylene, polystyrene, polyvinyl acetate, nylon, polyester, polybutadiene, polybenzimidazole, polyacrylonitrile, epichlorohydrin, polysulfide, polyisoprene and polyethylene glycol.

Similarly to the gas barrier layer 50, the adhesive layer 30 may have a gas barrier function with respect to the gas 21. To impart the gas barrier function, a material used in the gas barrier layer 50 may be added to the adhesive layer 30.

The adhesive layer 30 may be formed by applying a composition including the adhesive material and optionally a solvent onto the photosensitive gas generation layer 20.

After the composition is applied, for example, the coating may be heated with a device such as a hot plate. The heating conditions are usually 20 to 200° C. and 1 to 600 seconds.

The thickness of the adhesive layer is selected appropriately in accordance with the size and type of the material to be attached. Excessively thin adhesive layers may exhibit poor adhesion, and thus the lower limit thickness may be usually 10 μm or more. Excessively thick adhesive layers may make it difficult to isolate the adherend, and thus the upper limit thickness may be usually 1 mm or less.

1-3. Adherends

Examples of the adherends 40 include biological substances such as stem cells including iPS cells and ES cells, somatic cells inductively differentiated from such stem cells, nucleic acids, proteins, sugar chains, peptides and groups (colonies) of these substances, and semiconductor chips having devices such as semiconductor devices.

The target substance 40 to be attached may be bonded to the adhesive layer 30 by an appropriate method selected in accordance with the type of the target substance 40. When, for example, the target substance 40 to be attached is a biological substance, the target substance may be carried on a medium such as water, a buffer solution or a gas onto the adhesive layer through a port connected to an external member such as an inlet disposed in the support.

After the target substance 40 is attached to the adhesive layer 30, the adherend 40 may be subjected to various treatments. When, for example, the adherend is a biological substance, the treatment may be cultivation. The treatment may be a general semiconductor processing such as photofabrication in the case of a semiconductor chip as the adherend.

2. Step (2)

In the step (2), a gas 21 is generated by the exposure of the photosensitive gas generation layer 20, and the support 100 and the stack 200 are separated from each other by the action of the gas 21.

The support 100 and the stack 200 are separated from each other in such a manner that the gas 21 generated by the exposure of the photosensitive gas generation layer 20 lifts the stack 200 away from the support 100 by means of its buoyancy.

The step (2) may be carried out simultaneously with the exposure in the step (1), or may be performed after the step (1).

Figure 6:
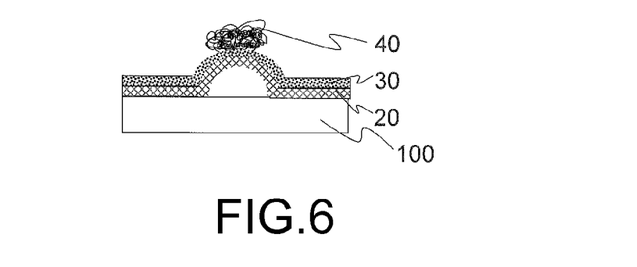
FIG. 6 is a schematic view illustrating an example of a process in which a portion of a stack is separated from a support.

The separation of the stack 200 from the support 100 may be partial separation of the stack as illustrated in FIG. 6.

To increase the buoyancy of the gas 21, the stack 200 may be heated with a device such as a hot plate. The heating conditions are usually 20 to 100° C. and 10 to 600 seconds in the case of biological substances as the adherends 40, and are usually 70 to 180° C. and 30 to 300 seconds for semiconductor chips as the adherends 40. To enhance the buoyancy of the gas 21, the support 100 and the stack 200 may be vibrated by a method such as the application of ultrasonic waves.

3. Step (3)

In the step (3), the adherend 40 is recovered from the support 100 by recovering the stack 200.

The adherend 40 is recovered by recovering the stack 200 that has been separated from the support 100 in the step (2). The recovery of the adherend 40 in the form of the stack 200 allows the adherend to be recovered from the support 100 efficiently and also prevents the adherend 40 from being reattached to the support 100.

The manner in which the recovery is performed may be selected appropriately in accordance with the type of the adherend 40. When, for example, the adherend 40 is a biological substance, the stack may be recovered together with a medium such as water, a buffer solution or a gas through a port connected to an external member such as an outlet disposed in the support.

The step (3) may be carried out simultaneously with the separation in the step (2), or after the step (2), or simultaneously with the steps (1) and (2).

After the recovery of the adherend 40, the adherend 40 may be isolated by separating the adherend 40 and the adhesive layer 30 from each other. The separation method may be selected appropriately in accordance with the type of the adherend 40. When, for example, the adherend 40 is a biological substance, the adherend 40 may be isolated by decomposing the adhesive layer 30 and molecules involved in the bonding between the adhesive layer 30 and the adherend 40 by the use of enzymes such as proteolytic enzymes and collagenolytic enzymes.

In the adherend recovery method of the invention, an adherend may be recovered with, for example, an apparatus (an adherend recovery apparatus) including the following members (1) to (6):

(1) a substrate (hereinafter, also written as "adherend recovery substrate") that includes a stack having a support, a photosensitive gas generation layer and an adhesive layer in this order, (2) a stage on which the substrate is placed, (3) a device configured to supply a target substance to the substrate, (4) a detection device configured to provide information of the position of the adherend, (5) an exposure device configured to expose the photosensitive gas generation layer, and (6) a control device configured to control the members (1) to (5).

In addition to the above members, the apparatus may include a device that identifies the adherend. When, for example, the adherend is a biological substance, the identification device may be one including an irradiator that applies light with a harmless wavelength to the biological substance, and an imaging element that captures a fluorescent image produced by the irradiation of the biological substance.

4. Methods for Selectively Recovering Adherends

Figure 7:
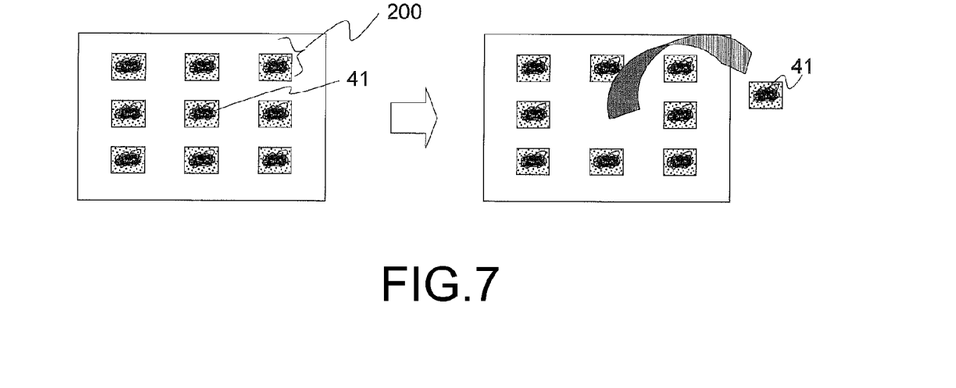
FIG. 7 is a schematic view illustrating a method for selectively recovering an adherend.

A method for selectively recovering an adherend utilizes the adherend recovery method of the invention. Specifically, the selective adherend recovery method is such that a plurality of stacks described above are disposed on the support and the desired adherend is selectively recovered from the support by selectively exposing the target stack. The selective adherend recovery method is schematically illustrated in FIG. 7.

The plurality of stacks 200 include at least two or more stacks 200. The stacks 200 may be arranged in any configuration. An exemplary configuration is a grid pattern illustrated in FIG. 7. Of the plurality of stacks 200, the stack 200 having the desired adherend 41 is selectively exposed and thereby the desired adherend 41 is recovered.

Examples of the exposure light usually used include ultraviolet rays and visible rays. Specifically, the light has a wavelength of 200 to 500 nm (for example, i-line wavelength (365 nm)) and may be selected appropriately in accordance with the type of the photosensitive gas generation layer. The exposure light may be laser light or may include a plurality of wavelengths. The active light irradiation dose may be selected appropriately in accordance with factors such as the type and thickness of the photosensitive gas generation layer. When the i-line wavelength is used as the exposure light, the exposure dose is usually 100 to 1500 mJ/cm$^2$.

The stack 200 of interest may be selectively exposed individually or, for example, exposure may be applied through a mask having an opening only in the region corresponding to the desired stack 200. For example, exposure may be applied with use of a contact aligner, a stepper or a scanner.

After being recovered by the selective adherend recovery method, the adherend 41 may be isolated by separating the adherend 41 and the adhesive layer from each other in the similar manner as described above.

The adherend(s) 40 that is not recovered by the selective adherend recovery method may be isolated by separating the adherend 40 and the adhesive layer from each other similarly to the adherend of interest.

Further, the stack(s) 200 that remains on the support 100 after the selective adherend recovery method has been performed may be used as a substrate having the adherend(s) 40 at an appropriate position(s) on the support 100. For example, such substrates having biological substances as the adherends 40 may be used as cell sensor substrates.

EXAMPLES

Preparation Examples 1 to 15

Compositions of Preparation Examples 1 to 15 were prepared by dissolving the binder resins and the photosensitive gas generators described in Table 1 in the solvents described in Table 1 so that the solid concentration would be 10 mass %. In Table 1, the term "parts" means parts by mass. Details of the components shown in Table 1 are as described below.

PMMA: polymethacrylic acid, weight average molecular weight 120,000

RB810: butadiene rubber, product name "RB810", manufactured by JSR CORPORATION, weight average molecular weight 230,000

Azido compound 1: condensate formed between 1 mole of a compound represented by Formula (1) below and 2.5 moles of 1,2-naphthoquinonediazido-5-sulfonic acid

[Chem. 1]

(1)

Azido compound 2: condensate formed between 1 mole of the compound represented by Formula (1) above and 4 moles of 1,2-naphthoquinonediazido-5-sulfonic acid Azido compound 3: condensate formed between 1 mole of a compound represented by Formula (2) below and 3.5 moles of 1,2-naphthoquinonediazido-5-sulfonic acid

[Chem. 2]

(2)

Azido compound 4: condensate formed between 1 mole of the compound represented by Formula (2) above and 4 moles of 1,2-naphthoquinonediazido-5-sulfonic acid Azide 1: compound represented by Formula (3) below:

[Chem. 3]

(3)

TABLE 1

| Prep. Ex. | Binder resins | | Photosensitive gas generators | | Solvents Types |
|---|---|---|---|---|---|
| | Types | Contents | Types | Contents | |
| 1 | PMMA | 100 Parts | Azido compound 1 | 5 Parts | Ethyl lactate |
| 2 | PMMA | 100 Parts | Azido compound 1 | 10 Parts | Ethyl lactate |
| 3 | PMMA | 100 Parts | Azido compound 1 | 20 Parts | Ethyl lactate |
| 4 | PMMA | 100 Parts | Azido compound 2 | 5 Parts | Ethyl lactate |
| 5 | PMMA | 100 Parts | Azido compound 2 | 10 Parts | Ethyl lactate |
| 6 | PMMA | 100 Parts | Azido compound 2 | 20 Parts | Ethyl lactate |
| 7 | PMMA | 100 Parts | Azido compound 3 | 5 Parts | Ethyl lactate |
| 8 | PMMA | 100 Parts | Azido compound 3 | 10 Parts | Ethyl lactate |
| 9 | PMMA | 100 Parts | Azido compound 3 | 20 Parts | Ethyl lactate |
| 10 | PMMA | 100 Parts | Azido compound 4 | 5 Parts | Ethyl lactate |
| 11 | PMMA | 100 Parts | Azido compound 4 | 10 Parts | Ethyl lactate |
| 12 | PMMA | 100 Parts | Azido compound 4 | 20 Parts | Ethyl lactate |
| 13 | RB810 | 100 Parts | Azide 1 | 10 Parts | Tetrahydrofuran |
| 14 | RB810 | 100 Parts | Azide 1 | 20 Parts | Tetrahydrofuran |
| 15 | PMMA | 100 Parts | Azide 1 | 10 Parts | Tetrahydrofuran |

Experiment Example 1

Figure 8:
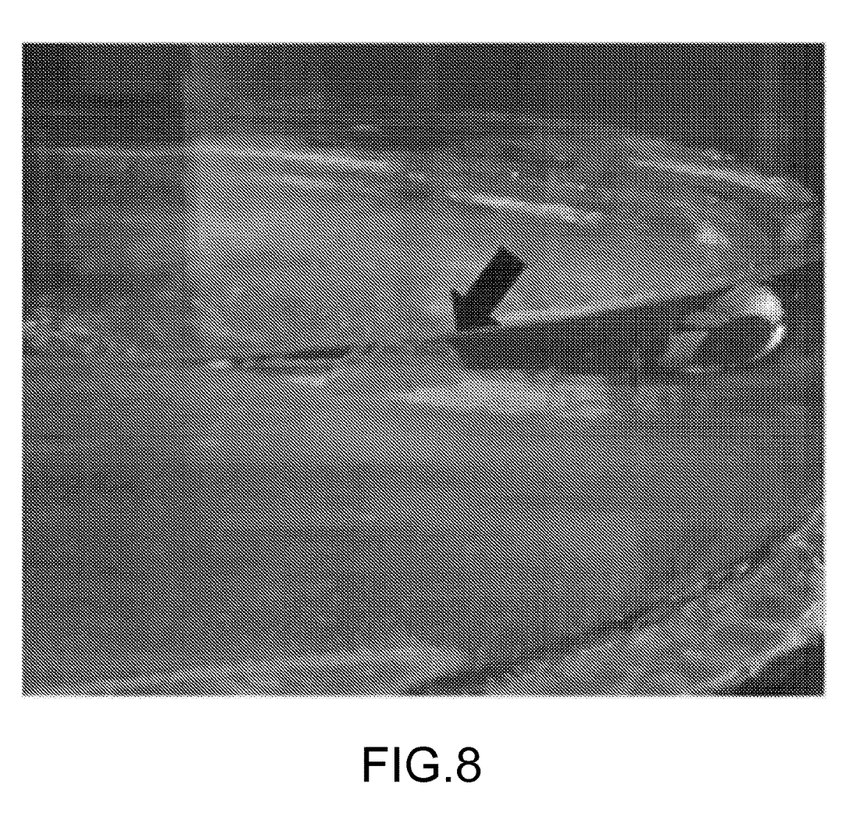
FIG. 8 is a photograph showing a stack separated from a glass plate in Experiment Example 1.

The composition of Preparation Example 1 was spin coated onto a glass plate, and the coating was heated on a hot plate at 110° C. for 5 minutes to form a film (a photosensitive gas generation layer) having a thickness of 10 μm. On the photosensitive gas generation layer, a vitronectin film as an adhesive layer was formed with a thickness of 50 μm. Normal human skin fibroblastic cells (manufactured by Dainippon Pharmaceutical Co., Ltd.) as an adherend were attached onto the adhesive layer. In this manner, a stack was formed in which the photosensitive gas generation layer, the adhesive layer and the adherend were stacked in this order on the glass plate. Through the glass plate, the entire surface of the stack was exposed (with a high-pressure mercury lamp). The exposure dose was 2,000 mJ/cm$^2$ at a wavelength of 430 nm. After the exposure, the glass plate and the stack were immersed in water. After the immersion, the stack was found to have been separated from the glass plate. FIG. 8 is a photograph showing the stack separated from the glass plate.

Experiment Examples 2 to 17

The procedures in [Experiment Example 1] were repeated except that the conditions were changed as described in Table 2 below, and the separation of the stack from the glass plate was checked. The results are set forth in Table 2.

TABLE 2

| Exp. Ex. | Compositions used to form photosensitive gas generation layers | Conditions in formation of photosensitive gas generation layers | Thicknesses of photosensitive gas generation layers | Separation of stacks from glass plates after immersion |
|---|---|---|---|---|
| 1 | Composition of Prep. Ex. 1 | 110° C. on hot plate for 5 min | 10 μm | Separated |
| 2 | Composition of Prep. Ex. 2 | 110° C. on hot plate for 5 min | 10 μm | Separated |
| 3 | Composition of Prep. Ex. 3 | 110° C. on hot plate for 5 min | 10 μm | Separated |
| 4 | Composition of Prep. Ex. 4 | 110° C. on hot plate for 5 min | 10 μm | Separated |
| 5 | Composition of Prep. Ex. 5 | 110° C. on hot plate for 5 min | 10 μm | Separated |
| 6 | Composition of Prep. Ex. 6 | 110° C. on hot plate for 5 min | 10 μm | Separated |
| 7 | Composition of Prep. Ex. 7 | 110° C. on hot plate for 5 min | 10 μm | Separated |
| 8 | Composition of Prep. Ex. 8 | 110° C. on hot plate for 5 min | 10 μm | Separated |
| 9 | Composition of Prep. Ex. 9 | 110° C. on hot plate for 5 min | 10 μm | Separated |
| 10 | Composition of Prep. Ex. 10 | 110° C. on hot plate for 5 min | 10 μm | Separated |
| 11 | Composition of Prep. Ex. 11 | 110° C. on hot plate for 5 min | 10 μm | Separated |
| 12 | Composition of Prep. Ex. 12 | 110° C. on hot plate for 5 min | 10 μm | Separated |
| 13 | Composition of Prep. Ex. 13 | 70° C. on hot plate for 10 min | 10 μm | Separated |
| 14 | Composition of Prep. Ex. 14 | 70° C. on hot plate for 10 min | 10 μm | Separated |
| 15 | Composition of Prep. Ex. 15 | 70° C. on hot plate for 10 min | 10 μm | Separated |
| 16 | Composition of Prep. Ex. 15 | 70° C. on hot plate for 10 min | 5 μm | Separated |
| 17 | Composition of Prep. Ex. 15 | 70° C. on hot plate for 10 min | 1 μm | Separated |

The invention claimed is:

1. An adherend recovery method for recovering an adherend from a support, comprising:
a step (I) of exposing a stack disposed on the support, the stack including a photosensitive gas generation layer, an adhesive layer and the adherend in this order on the support, a step (II) of generating a gas from the photosensitive gas generation layer to separate the support and the stack from each other by the action of the gas, and a step (III) of recovering the adherend from the support by recovering the stack separated,
wherein the adherend is a biological cell.

2. The adherend recovery method according to claim 1, wherein the photosensitive gas generation layer includes at least one selected from azides and diazo compounds.

3. The adherend recovery method according to claim 1, wherein the photosensitive gas generation layer includes an elastomer.

4. The adherend recovery method according to claim 1, wherein the photosensitive gas generation layer includes a polymer containing a (meth)acrylic structural unit.

5. The adherend recovery method according to claim 4, wherein the photosensitive gas generation layer comprises 5 to 20 parts by mass of the at least one selected from azides and diazo compounds based on 100 parts by mass of the polymer containing a (meth)acrylic structural unit.

6. The adherend recovery method according to claim 1, wherein a plurality of stacks are disposed on the support and a desired adherend is selectively recovered from the support by selectively exposing the target stack.

* * * * *